United States Patent
Duran et al.

(10) Patent No.: US 6,491,511 B1
(45) Date of Patent: Dec. 10, 2002

(54) MOLD TO FORM STENT-LESS REPLACEMENT HEART VALVES FROM BIOLOGICAL MEMBRANES

(75) Inventors: Carlos M. G. Duran, Missoula, MT (US); Joon Hock Yeo, Singapore (SG)

(73) Assignee: The International Heart Institute of Montana Foundation, Missoula, MT (US)

( * ) Notice: Subject to any disclaimer, the term of this patent is extended or adjusted under 35 U.S.C. 154(b) by 0 days.

(21) Appl. No.: 09/418,675

(22) Filed: Oct. 14, 1999

(51) Int. Cl.⁷ .................................. A61F 2/24
(52) U.S. Cl. ............... 425/394; 425/496; 623/2.15
(58) Field of Search ............... 425/387.1, 388, 425/394, 446; 623/2.15

(56) References Cited

U.S. PATENT DOCUMENTS

| | | | |
|---|---|---|---|
| 3,320,972 A | * 5/1967 | High et al. | 137/844 |
| 3,655,306 A | * 4/1972 | Ross et al. | 425/521 |
| 4,218,782 A | * 8/1980 | Rygg | 623/2.15 |
| 4,473,423 A | * 9/1984 | Kolff | 156/245 |
| 4,692,164 A | 9/1987 | Dzemeshkevich et al. | 623/2 |
| 5,344,442 A | 9/1994 | Deac | 623/2.12 |
| 5,425,741 A | 6/1995 | Lemp et al. | 606/167 |
| 5,489,298 A | 2/1996 | Love et al. | 623/2.14 |
| 5,500,015 A | 3/1996 | Deac | 606/167 |
| 5,509,930 A | 4/1996 | Love | 623/2.1 |
| 5,522,885 A | 6/1996 | Love et al. | 623/2.11 |
| 5,531,784 A | 7/1996 | Love et al. | 73/37 |
| 5,531,785 A | 7/1996 | Love et al. | 623/2.11 |
| 5,571,174 A | 11/1996 | Love et al. | 29/890.12 |
| 5,584,878 A | 12/1996 | Love et al. | 623/913 |
| 5,588,967 A | 12/1996 | Lemp et al. | 606/167 |
| 5,609,600 A | 3/1997 | Love et al. | 606/167 |
| 5,612,885 A | 3/1997 | Love | 623/2.1 |
| 5,653,749 A | 8/1997 | Love et al. | 128/898 |
| 5,662,705 A | 9/1997 | Love et al. | 128/898 |
| 5,697,382 A | 12/1997 | Love et al. | 128/898 |
| 5,716,399 A | 2/1998 | Love | 128/898 |
| 5,885,228 A | 3/1999 | Rosenman et al. | 600/587 |

FOREIGN PATENT DOCUMENTS

WO    98/32401    7/1998    ............. A61F/2/24

OTHER PUBLICATIONS

Duran et al., From Aortic Cusp Extension to Valve Replacement with Stentless Pericardium (unstented, shaped) Annal Thoracic Surgery, 1995, 60: S428–32.

Duran et al., Aortic Valve Replacement with Freehand Autologous Pericarium (unstented, shaped) Journal of Thoracic and Cardiovascular Surgery Aug. 1995.

Duran et al., Aortic Valve Replacement with Autologous Pericardium (unstented, shaped) Surgical Technique Journal of Cardiovascular Surgery 1995, 10:1–19.

(List continued on next page.)

Primary Examiner—Jan H. Silbaugh
Assistant Examiner—Thu Khanh T. Nguyen
(74) Attorney, Agent, or Firm—Gabor L. Szekeres (57) ABSTRACT

A pair of templates form a mold for substantially flat biological membranes to shape the membrane into a configuration that, after trimming of excess tissue, is adapted for forming a replacement aortic, pulmonary, tricuspid or mitral heart valve. Each template has three members joined to another laterally, with each member configured to form, together with its mating member, the mold for one leaflet or cusp of the replacement heart valve. The negative template has concave surfaces for each member and the positive template has convex surfaces which mate with the concave surfaces of the first template. Each of the templates is made of thin, shell like material and has beveled edges. The biological membrane is placed between the mating convex and concave surfaces of the two templates assembled to one another to form the membrane into the configuration of the three leaflets of the replacement heart valve.

20 Claims, 11 Drawing Sheets

OTHER PUBLICATIONS

Love, Antologous Pericardial Reconstruction of Semilunar Valves Journal of Heart Valve Disease 1998, vol. 7 No. 1.

Senning A., Facscia Lata Replacement of Aortic Valves (unstented, unshaped) Journal of Thoracic Cardiovascular Surgery 1967, 54: 465–470.

Edwards et al., Mitral and Aortic Valve Replacement with Fascia Lata on a Frame (stented, unshaped) Journal of Thoracic Cardiovascular Surgery 1969, 58: 854–858.

Yacoub et al., Aortic Valve Replacement Using Unstented Dura or Calf Pericardium: Early and Medium Term Results in Biologic Bioprosthetic Valves (unstented, unshaped) Proceedings of the Third International Symposium. In: Bodnar E. Yacoub m (ed) Yorke Medical Books, New York 1986: 684–690.

Batista et al., Clinical Experience with Stentless Pericardium Aortic Monopatch for Aortic Valve Replacement (unstented, unshaped) Journal of Thoracic and Cardiovascular Surgery 1987: 93: 19–26.

* cited by examiner

MOLD TO FORM STENT-LESS REPLACEMENT HEART VALVES FROM BIOLOGICAL MEMBRANES

BACKGROUND OF THE INVENTION

1. Field of the Invention

The present invention is in the field of equipment and devices related to manufacturing heart valves to be used in cardiac surgery. More specifically, the present invention is directed to molds in which biological membranes are shaped into the configuration of replacement heart valves to be used in cardiac surgery. The present invention is also directed to a sizer for measuring the valve annulus of a patient so as to determine the appropriate size of mold to be used in that patient.

2. Brief Description of the Prior Art

Heart valve reconstruction using patient's own tissue (autologous tissue) or cadaver (homologous) or animal (heterologous) tissue is not new. As is known, heart valves (aortic, pulmonary, tricuspid or mitral) function essentially as check valves which operate hemodynamically in synchronization with the pumping action of the heart, allowing blood flow in a downstream direction and blocking flow in the opposite or upstream direction. One of the important requirements in valve reconstruction using autologous, homologous or heterologous tissue is the ability to produce a valve form which is as close to the natural valve as possible in order to serve its function effectively as a replacement valve. In addition it is important to fabricate the replacement valve accurately to fit any specific patient, quickly and effectively within the shortest possible time frame.

Among the tissues used in these molds for fabricating replacement heart valves, autologous tissue has been given special consideration because of its low cost, availability from the patient who is undergoing the open heart surgery operation, and relative ease of handling. For the ultimate replacement valve design, however, the nature of the mold in which the valve is formed is also of great importance, and over the years, a number of molds or templates were introduced to fabricate replacement heart valves from autologous, homologous or heterologous tissue. As noted above, the replacement valve should mimic the natural heart valve as close as possible. As a summary of prior art valve design, the following developments are noted.

Duran et al. Journal of Thoracic and Cardiovascular Surgery, 1995, August have developed a valve mold comprising 3 bulges or lobes in a rectangular plastic container. The bulges serve to reproduce the 3 leaflets of the aortic valve. A strip of autologous pericardium is laid over the bulges and an opposite mold to the 3 bulges is held over the pericardial strip whilst immersed in a solution containing a tanning agent that fixes the pericardium strip in the shape dictated by the mold. After fixation, the pericardial strip is removed and is held in the surgeon's hand for trimming along the impression left by the mold. Trimming of the unsupported autologous tissue, which is flimsy and thus difficult to handle results in certain inaccuracy in tracing the path marked by the mold.

Love et al. Journal of Heart Valve Disease 1998, Volume 7, No. 1. have designed a valve mold with a concept similar to the above-described, involving a positive and a negative template and having an added feature of a "cutter" to trim the excess autologous tissue while the tissue is held in the mold. The Love et al. Journal of Heart Valve Disease 1998, Volume 7, No. 1. valve mold is constructed primarily of metal which makes the overall device heavy and relatively bulky.

Generally speaking, the two main problems which can be identified in current state-of-the-art valve mold design are:

(i) Difficulty in trimming the excess pericardium effectively, accurately within shortest possible time, and (ii) the overall design of the valve mold is heavy and or bulky.

In light of the foregoing, there is a need in the state-of-the-art for a mold design for valves that offers greater precision and reproducibility to overcome the above-stated problems, and is cost effective in manufacturing.

Written descriptions of examples of prior art valve mold design and of the procedures employed by the surgeon in the operating room are found in U.S. Pat. Nos. 5,344,442; 5,425,741; 5,489,298; 5,500,015; 5,509,930; 5,522,885; 5,531,784; 5,531,785; 5,571,174; 5,584,878; 5,588,967; 5,609,600; 5,612,885; 5,653,749; 5,662,705; 5,697,382, and 5,716,399. Many of the valve constructions described in these patents include valve stents that are needed to support the molded tissue to form the replacement valve.

The following scientific publications also describe or relate to the use of human or animal membranes for heart valve replacement.

1. Senning A. Fascia Lata Replacement of Aortic Valves (unstented, unshaped) Journal of Thoracic Cardiovascular Surgery 1967, 54:465–470;
2. Edwards et al. Mitral and Aortic Valve Replacement with Fascia Lata on a Frame (stented, unshaped) Journal of Thoracic Cardiovascular Surgery 1969, 58:854–858;
3. Yacoub et al Aortic Valve Replacement Using Unstented Dura or Calf Pericardium: Early and Medium Term Results in Biologic Bioprosthetic Valves (unstented, unshaped) Proceedings of the third international symposium. In: Bodnar E, Yacoub m (ed) Yorke Medical books, New York 1986:684–690;
4. Batista et al. Clinical Experience with Stentless Pericardium Aortic Monopatch for Aortic Valve Replacement (unstented, unshaped) Journal of Thoracic and Cardiovascualr Surgery 1987:93:19–26;
5. Duran et al. From Aortic Cusp Extension to Valve Replacement with Stentless Pericardium (unstented, shaped) Annal Thoracic Surgery, 1995, 60:S428–32;
6. Duran et al. Aortic Valve Replacement with Freehand Autologous Pericardium (unstented, shaped) Journal of Thoracic and Cardiovascular Surgery 1995 August;
7. Duran et al. Aortic Valve Replacement with Autologous Pericardium (unstented, shaped) Surgical Technique Journal of Cardiovascular Surgery 1995, 10:1–19;
8. Love Autologous Pericardial Reconstruction of Semilunar Valves Journal of Heart Valve Disease 1998, Vol 7 No. 1;

SUMMARY OF THE INVENTION

It is an object of the present invention to provide a mold that is suitable for rapidly forming a substantially flat biological membrane into a configuration that can be quickly and accurately trimmed to provide a replacement heart valve.

It is another object of the present invention to provide a mold that satisfies the foregoing objective and allows formation of the replacement heart valve with high accuracy and repeatability.

It is still another object of the present invention to provide a mold that satisfies the foregoing objectives and is relatively easy and economical to manufacture and handle.

It is yet another object of the present invention to provide a set of sizers to measure accurately the diameter of the aortic valve annulus of the patient in order to determine and select the appropriate size of mold to be used in that particular patient.

The foregoing and other objects and advantages are attained by a pair of templates provided to form a mold for substantially flat biological membranes such as a pericardium, peritonium or pleura, to shape the membrane into a configuration that, after trimming of excess tissue, is adapted for forming a replacement aortic, pulmonary, tricuspid or mitral heart valve. Each template of the pair has three members joined to another laterally, with each member configured to form, together with its mating member, the mold for one leaflet or cusp of the replacement heart valve. The first or negative template has concave surfaces for each member and the second or positive template has convex surfaces which mate with the concave surfaces of the first template. Each of the templates is made of thin, shell like material and has thin edges that makes it easy to cut with a surgical knife close to the mold. The biological membrane is placed between the mating convex and concave surfaces of the two templates assembled to one another to form the membrane into the configuration of the three leaflets of the replacement heart valve. The templates of the mold are provided with apertures to allow a liquid composition to percolate to the membrane and affix the membrane in the configuration defined by the mold.

DESCRIPTION OF THE PREFERRED EMBODIMENTS

The following specification taken in conjunction with the drawings sets forth the preferred embodiments of the present invention. The embodiments of the invention disclosed herein are the best modes contemplated by the inventors for carrying out their invention in a commercial environment, although it should be understood that various modifications can be accomplished within the parameters of the present invention.

Figure 26:
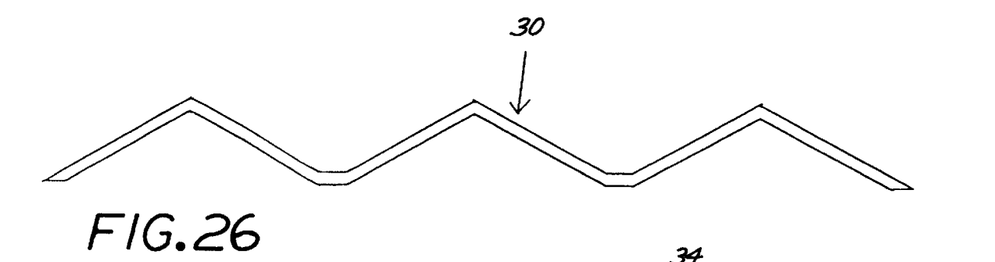
FIG. 26 is a front plan view of the second preferred embodiment of the negative template of FIG. 25.
Figure 27:
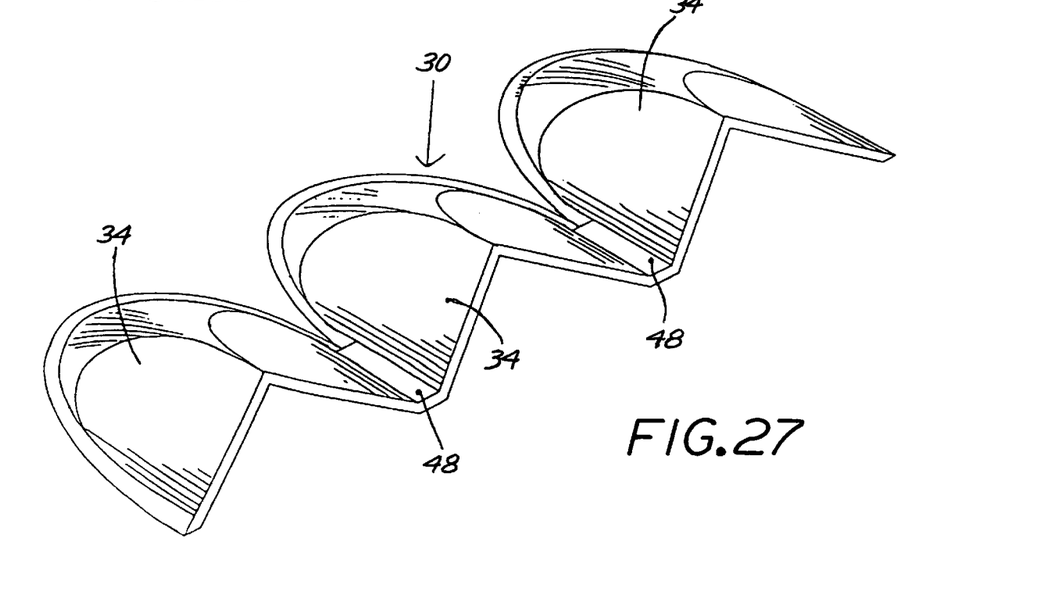
FIG. 27 is a schematic perspective view of the second preferred embodiment of the negative template of FIG. 25.
Figure 28:
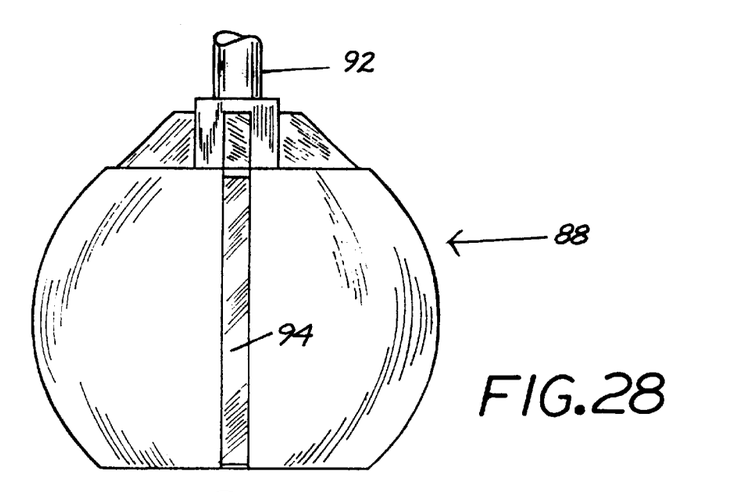
FIG. 28 is a plan view of a first preferred embodiment of a valve sizer in accordance with another aspect of the present invention.
Figure 29:
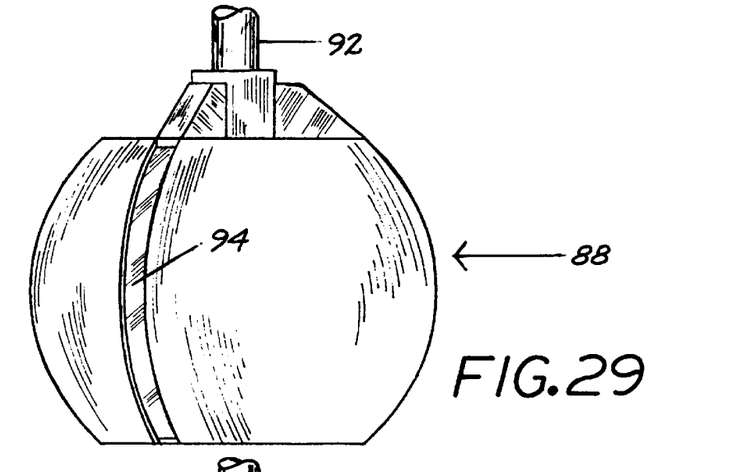
FIG. 29 is another plan view of the first preferred embodiment of the valve sizer.
Figure 30:
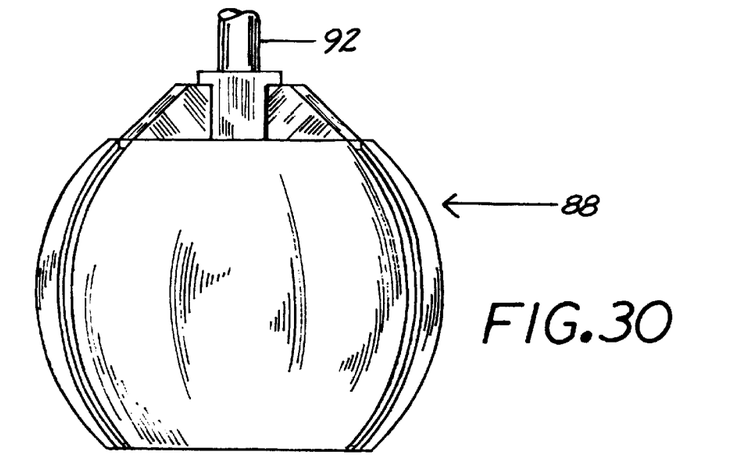
FIG. 30 is still another plan view of the first preferred embodiment of the valve sizer.
Figure 31:
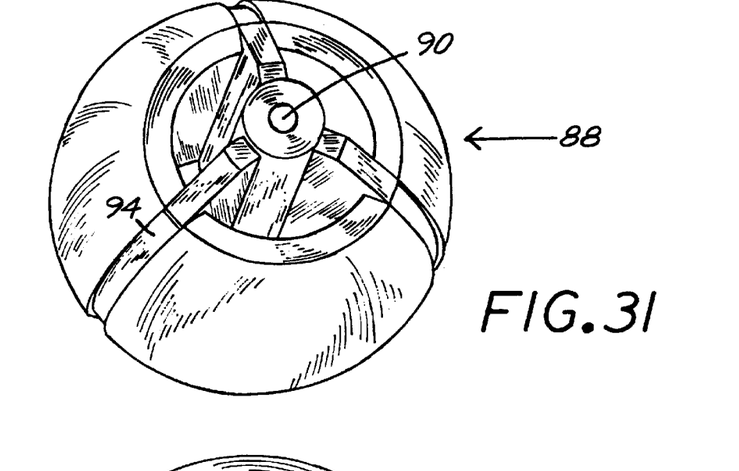
FIG. 31 is a perspective view of the first preferred embodiment of the valve sizer.
Figure 32:
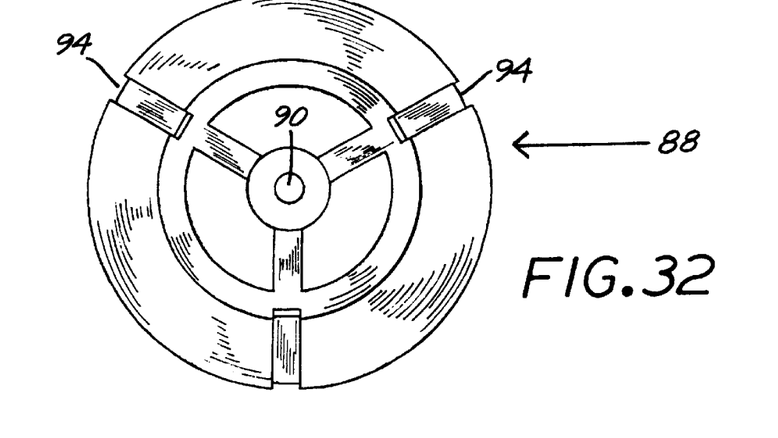
FIG. 32 is a top plan view of the first preferred embodiment of the valve sizer.
Figure 33:
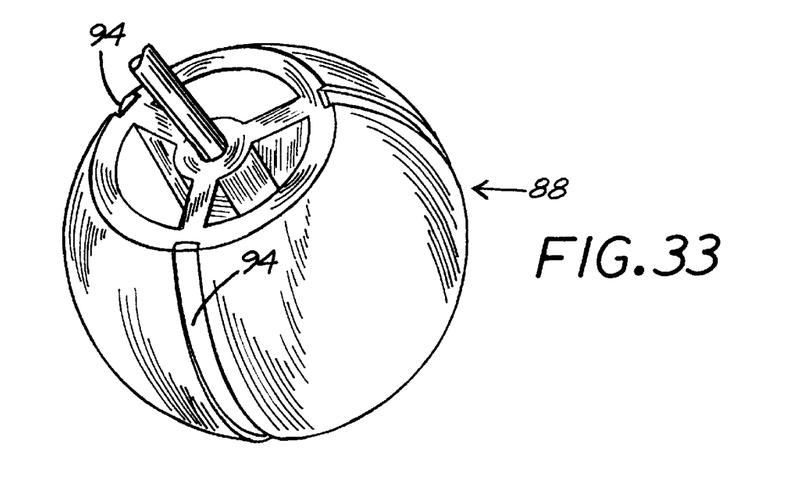
FIG. 33 is another perspective view of the first preferred embodiment of the valve sizer.

Referring now to the drawing figures, a mold for forming heart replacement valves from biological membranes is disclosed. It should be noted at the outset that molds for forming aortic, pulmonary, tricuspid and mitral replacement valves can be provided in accordance with the present invention. It should also be noted that autologous, homologous and heterologous biological membranes, such as the peritonium, pericardium and pleura are suitable to be used in the molds of the present invention to form the above noted replacement heart valves. FIGS. 1–8 schematically illustrate without all details of an actual fabricated embodiment, the general geometry and configuration of a mold for forming aortic heart valve replacements. An exemplary first preferred embodiment of an actual mold for forming pericardial heart valve replacements is schematically illustrated in FIGS. 9–24, and the invention is described below primarily with reference to the schematic illustration of FIGS. 1–8 and the first preferred embodiment shown in FIGS. 9–24. An exemplary second preferred embodiment is illustrated in FIGS. 26–28.

Figures 1, 2, 3, 4, 5:
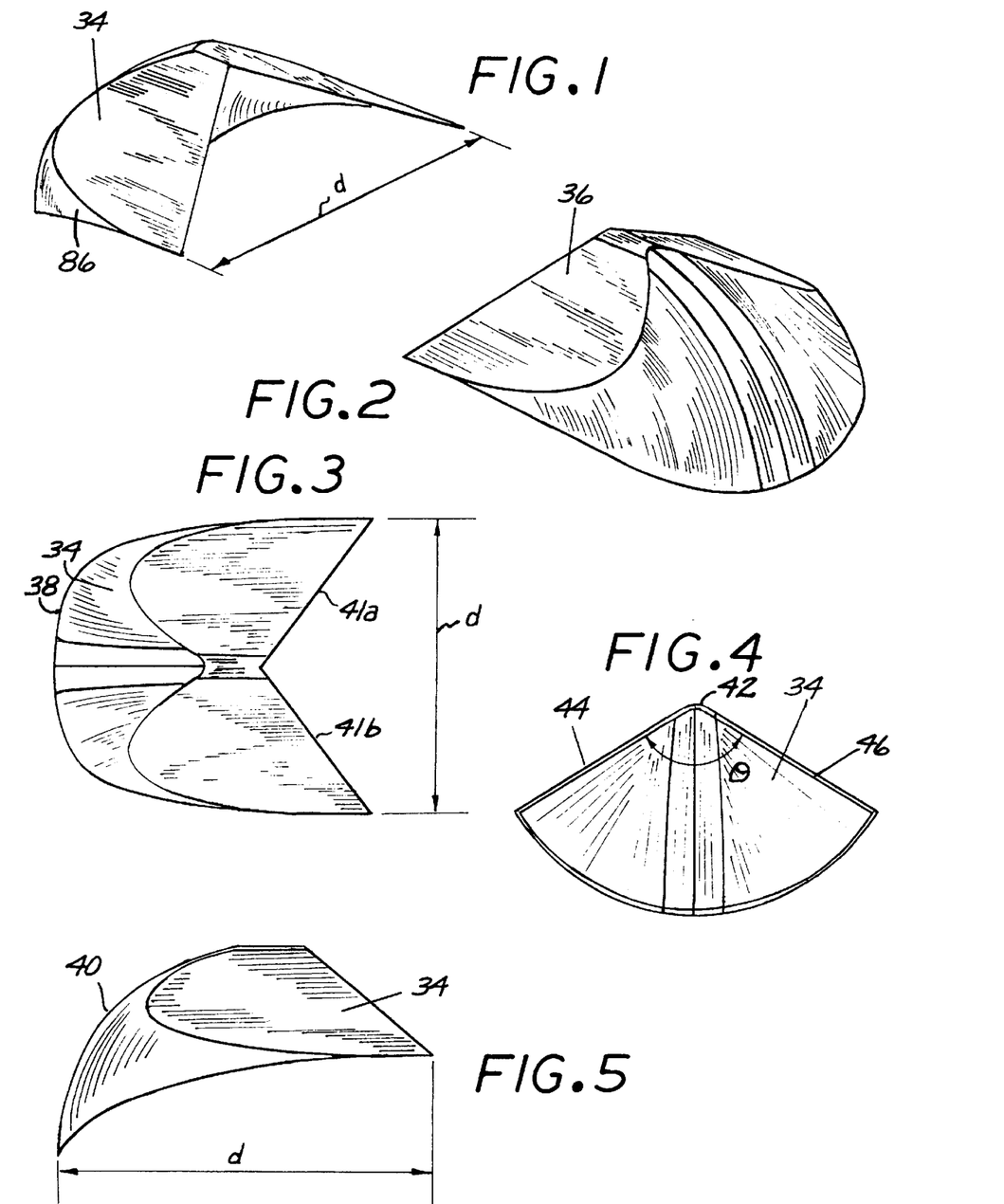
FIG. 1 is a schematic perspective view showing the general configuration of one cusp of a negative template of a mold used for shaping an aortic valve replacement from autologous tissue, utilizing the novel solution and method of the present invention.
FIG. 2 is a schematic perspective view showing the general configuration of one cusp of a positive template of the mold used for shaping an aortic valve replacement from autologous tissue, utilizing the novel solution and method of the present invention.
FIG. 3 is a top plan view of the negative cusp of FIG. 1.
FIG. 4 is an end plan view of the negative cusp of FIG. 1.
FIG. 5 is a side plan view of the negative cusp of FIG. 1.

A principal feature of the molds of the present invention is that it comprises two thin templates having matching, complementary surfaces that mate with one another and that the joint mating surfaces of the two shell templates define the configuration and dimensions of the resulting heart valve replacement membrane. Thus, the mold schematically illustrated by its overall dimensions and configuration in FIGS. 1–8 includes a negative template 30 schematically shown in its entirety in FIGS. 6–8 and a positive template 32, one member or cusp 36 of which is schematically shown in FIG. 2. A perspective view of one member or cusp 34 of the negative template of the herein described aortic mold is shown in FIG. 1.

The templates 30 and 32 are made of sufficiently thin material that when the templates are assembled their joint thickness does not substantially exceed 4 mm. The thickness of the templates 30 and 32 is preferably in the range of approximately 0.5 to 2.5 mm. The templates 30 and 32 can be manufactured in the herein described configurations and dimensions from plastic materials, such as high density polyethylene, polypropylene, polyesters, polyamides and other suitable plastic materials, by plastic manufacturing techniques well known in the art, for example by injection molding in a suitable die (not shown). The template can also be made of resorbable material which would provide a platform or skeleton for cultured cells from autologous, homologous or heterologous origin to grow on and into it.

It should be already apparent from the foregoing description that the shape or configuration and dimensions of the templates 30 and 32, more precisely the shape and dimensions of their mating surfaces determine the configuration and dimensions of the heart valve that is molded in the templates. Keeping the foregoing in mind, and primarily with reference to the plan views of FIGS. 3, 4 and 5, the configuration and dimensions of the aortic valve negative template are illustrated. Because the templates are made of thin material where the thickness of the material is substantially uniform and insignificant relative to the overall size of the template, therefore the illustrated surface of each template in the drawing figures also substantially illustrates with opposite concavity or convexity, as applicable, the general geometry of the other side of the template.

Thus, the curvature of the concave mating surface of the cusp 34 of the negative template 30 is such that the line 38 shown in the plan view of FIG. 3 is an ellipse described by the equation $$x^2/a^2 + y^2/b^2 = 1$$

where a has a value greater than zero and less than 22.0 (0<a<22.0), and b has a value greater than zero and less than 14.0 (0<b<14.0).

The curvature indicated with the line 40 in FIG. 5 in each cusp 34 of the negative template is also an ellipse described by the equation $$x^2/a^2 + z^2/c^2 = 1$$

where a has a value greater than zero and less than 14.0 (0<a<14.0), c has a value greater than zero and less than 12.0 (0<c<12.0), and x, y and z represent variables in the respective x, y and z axes of space.

The angle between the two lines 41a and 41b in FIG. 3 is α whose range is between approximately 90 to 115°.

The apex 42 of the template, as shown in the side plan view of FIG. 4 is formed between two straight lines 44 and 46 with an angle Θ. Angle Θ generally is in the range of approximately 110 to 120° to ensure proper valve closure such that the molded leaflets are in contact with one another. The preferred range for angle Θ is approximately 113 to 116°. Due to the angle Θ three leaflets of the heart valve molded and assembled in accordance with the present invention which are similar in form (although not necessarily in size) contact one another and provide perfect or substantially perfect closing of the heart valve. The overall dimension indicated with line d on FIGS. 1, 3 and 5 is between 0.8 d' to 1.0 d' (0.8d'<d<1.0d') where d' represents the diameter of the patient's valve root annulus. In this connection it is noted that several molds of varying sizes may be provided in accordance with the present invention to fit several patient's with varying heart valve root annulus dimensions, or that a mold can be fabricated to provide a heart valve that fits an individual patient. Height of the cusp 34 is determined by the dimension d, (which itself depends on the diameter (d') of the patient's valve root annulus) and by the angle of Θ formed at the apex of the equal-sided triangle shown in FIG. 4. In this connection, the values of the parameters a, b, c, and d are determined by the dimension of the heart valve replacement needed for any given patient, whether the mold for the valve is fabricated for the individual or is selected from among numerous available molds of varying sizes. As it will be readily understood by those skilled in the art of cardiology and related cardiac surgery, echocardiograms of the patient provide the information as to what size heart valve replacement is needed for that patient. It should be further understood in this connection that natural or native heart valves vary in sizes and that the three cusps of the native heart valve of a patient may not be of identical size. For this reason, a "tailor" made mold for an individual patient may not have equal size for each of the three cusps although each cusp would be described by the equation defined above just that the parameters a, b, c and d may have different values for each cusp. As noted above, the parameters a, b, c and d can be determined for each cusp from echocardiograms of the patient in order to make a custom or "tailor"-made mold and replacement heart valve.

Figure 6:
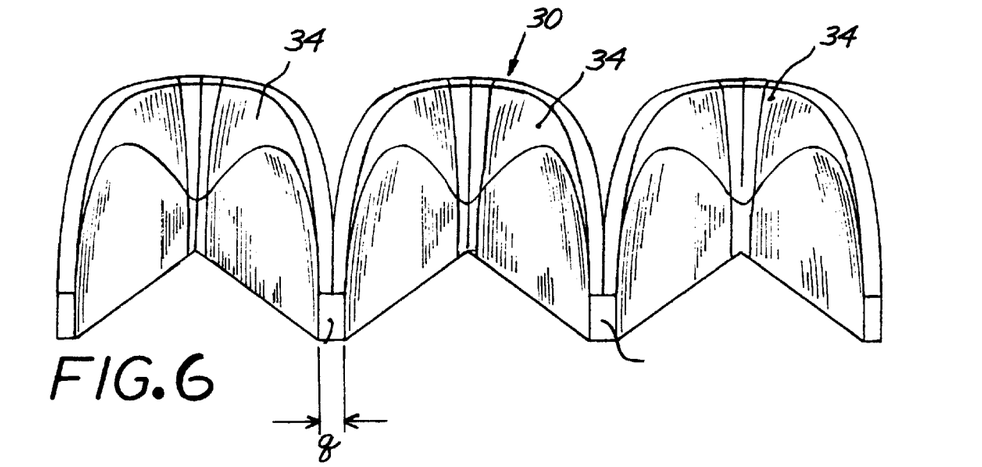
FIG. 6 is a schematic top plan view showing the general configuration of three negative cusps of FIG. 1 assembled to form a negative template used for shaping an aortic valve replacement from autologous tissue, utilizing the novel solution and method of the present invention.
Figure 7:
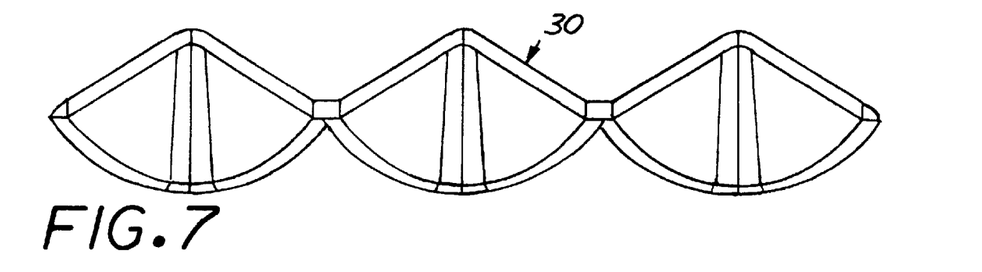
FIG. 7 is a front plan view of the negative template of FIG. 6.
Figure 8:
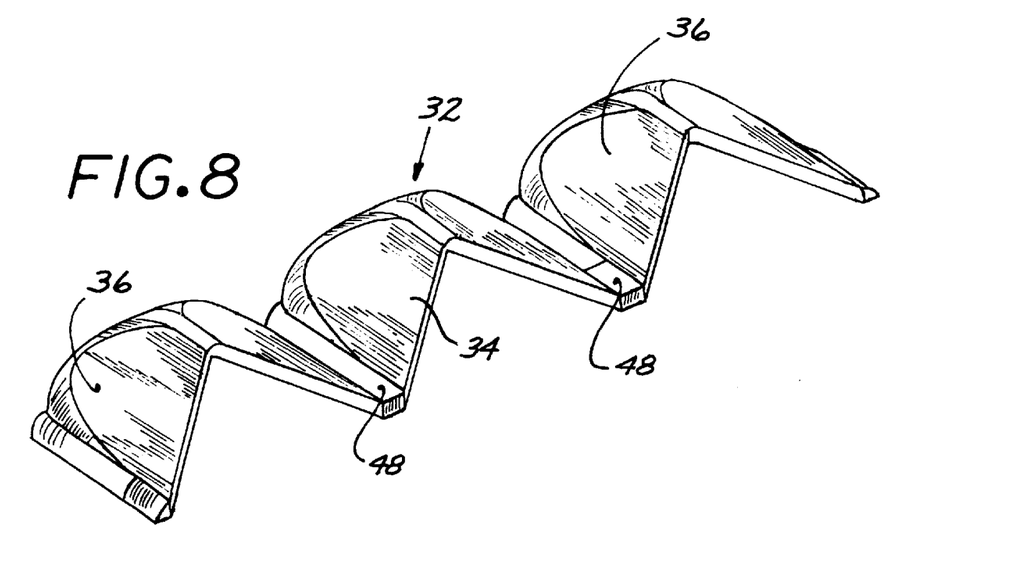
FIG. 8 is a schematic perspective view of the negative template of FIG. 6.

FIGS. 6, 7 and 8 schematically illustrate the overall dimensions and configuration of the negative template 30

"assembled" from three members or cusps 34 previously described and illustrated in FIGS. 1, 3, 4 and 5. Thus, the three cusps 34 are connected with small strips of substantially flat material whose width is indicated in FIG. 6 by the reference g. The width of these connecting strips 48 is between approximately 0.05 to 0.20 d' (0.05 d'<g<0.20 d'), where d' again represents the diameter of the patient's valve root annulus. The positive template (shown and described for the detailed embodiment below) has a configuration that provides a mating surface to the negative template 30. Those skilled in the plastic manufacturing and related arts will readily appreciate that the templates 30 and 32 are not necessarily physically assembled from the individual cusps, rather each template is preferably fabricated as a single integral unit, for example by an injection molding technique. The substantially flat connecting strips 48 provide flat areas in the resulting replacement heart valve where the heart valve can be sutured to the aortic root of the patient.

FIGS. 9 through 18 disclose a mold 52 for a pericardial heart valve replacement in more detail than the schematic views of FIGS. 1 through 8. It should be understood that the overall configurations and dimensions of the two templates of the mold 52 are as described above. However, certain features of the mold 52 are shown only in these detailed figures. FIGS. 9, 10, 11, and 15 illustrate the negative template 54 of the mold 52. The negative template 54 is an integrally fabricated (preferably by injection molding) thin shell of substantially uniform thickness. As described above in connection with the general geometry of the mold 52, the thin shell template 54 is comprised of three members or cusps 56 which are joined together with substantially flat narrow connecting strips 48. Through holes or perforations 58 are located evenly in the shell. The holes or perforations 58 allow a treating or tanning solution to penetrate through the mold 52 to a biological membrane (shown in FIGS. 19–24) which is placed into the mold 52. Grooves or indentations 60 which appear semi-circular in the top plan view are disposed in the negative template 54 at the highest and lowest points of the commissures or cusps 56. The grooves 60 mark the biological membrane tissue that is molded in the mold 54, and later guide the suturing process. A downward angle or bevel is also disposed in the edges 50 of the negative template 54 in its interior or lower surface that mates with the positive template shown in FIGS. 12–14 and 16. The angle or bevel of the edge 50 of the negative template 54 is shown in the break-away portion of FIG. 11. The angled or beveled edge which mate with the beveled edge 62 of the positive template 64 serves an important function by allowing the surgical knife or scissor to come very close to the tissue to effectively and accurately trace the profile of the valve mold as the knife or scissor trims the tissue sandwiched in the mold 52. Without this bevel or thin edge around the mold 52 the trimming of the sandwiched tissue would be difficult and inaccurate particularly at sharp comers.

In the negative template 54 a small gap or open space 66 is disposed between the cusps 56, leading to a hole or aperture 68 located at the highest point on the commissure or cusp 56. The gap 66 is wide enough to allow a surgical knife to pass through to make a cut up to the hole 68. The hole 68 allows the surgeon to identify the highest point in the membrane being molded. Two of the indentations or grooves 60 in the edge of the negative template 54 are in positions where they align with the hole 68 . These two grooves 60 also mark the highest point on the commissure.

Figures 9, 10, 11:
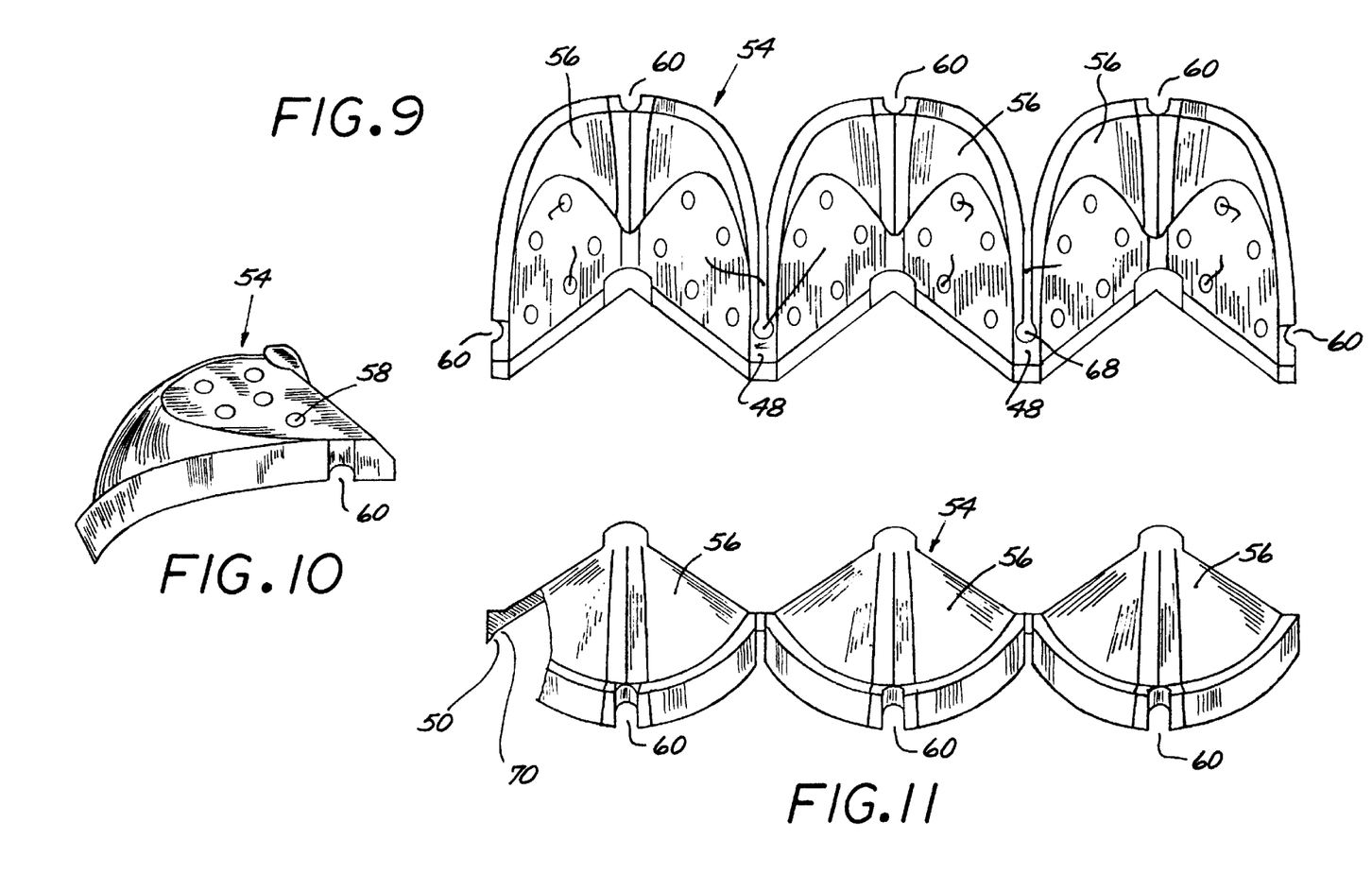
FIG. 9 is a detailed top plan view of a first preferred embodiment of a negative template used for shaping a pericardial valve replacement from autologous tissue, utilizing the novel solution and method of the present invention.
FIG. 10 is an end view of the first preferred embodiment of the negative template of FIG. 9.
FIG. 11 is a front plan view of the first preferred embodiment of the negative template of FIG. 9, with part of the front material broken away.
Figures 12, 13, 14:
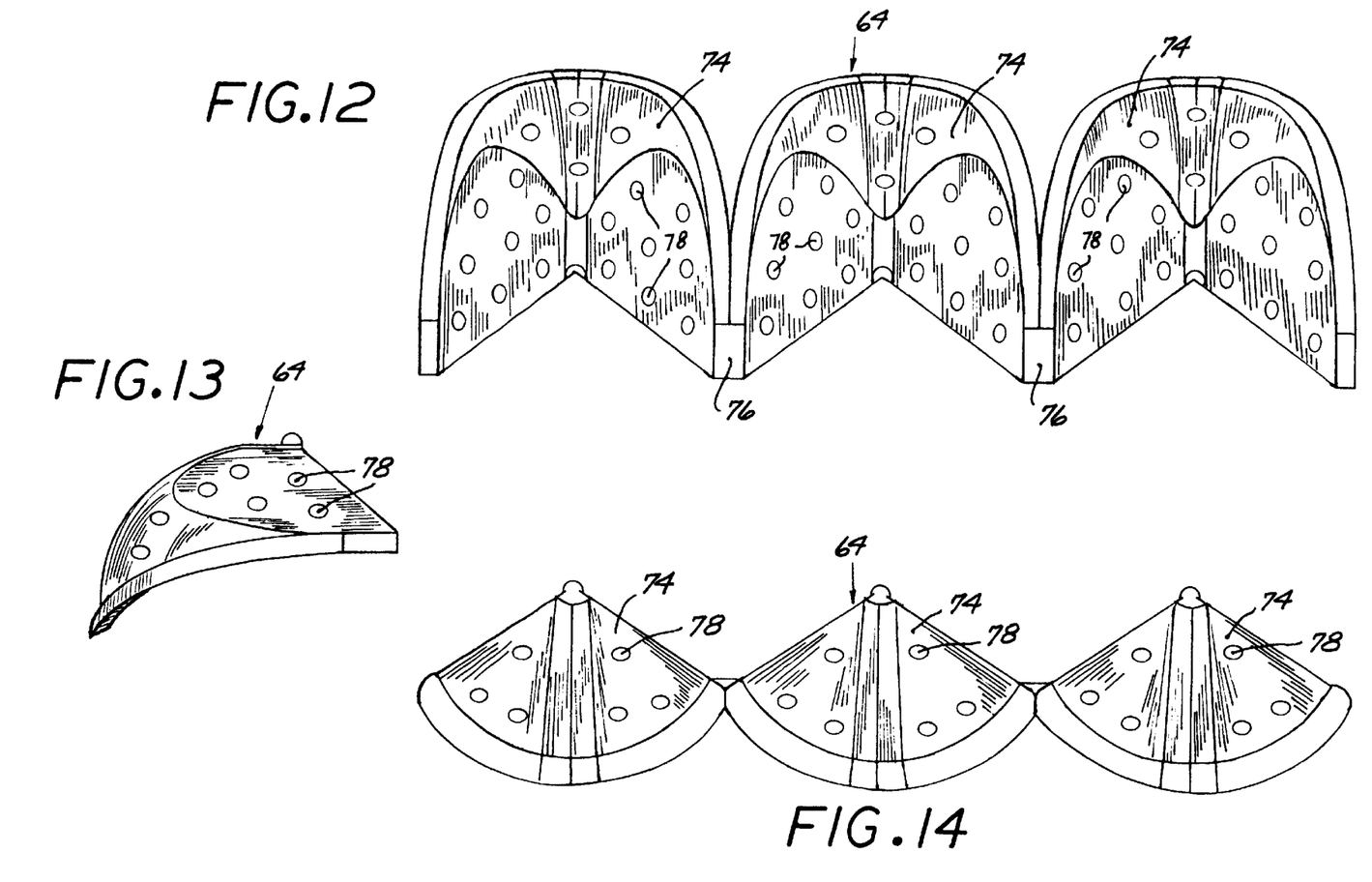
FIG. 12 is a detailed top plan view of a first preferred embodiment of a positive template used for shaping a pericardial valve replacement from autologous tissue, utilizing the novel solution and method of the present invention.
FIG. 13 is an end view of the first preferred embodiment of the positive template of FIG. 12.
FIG. 14 is a front view of the first preferred embodiment of the positive template of FIG. 12.
Figure 15:
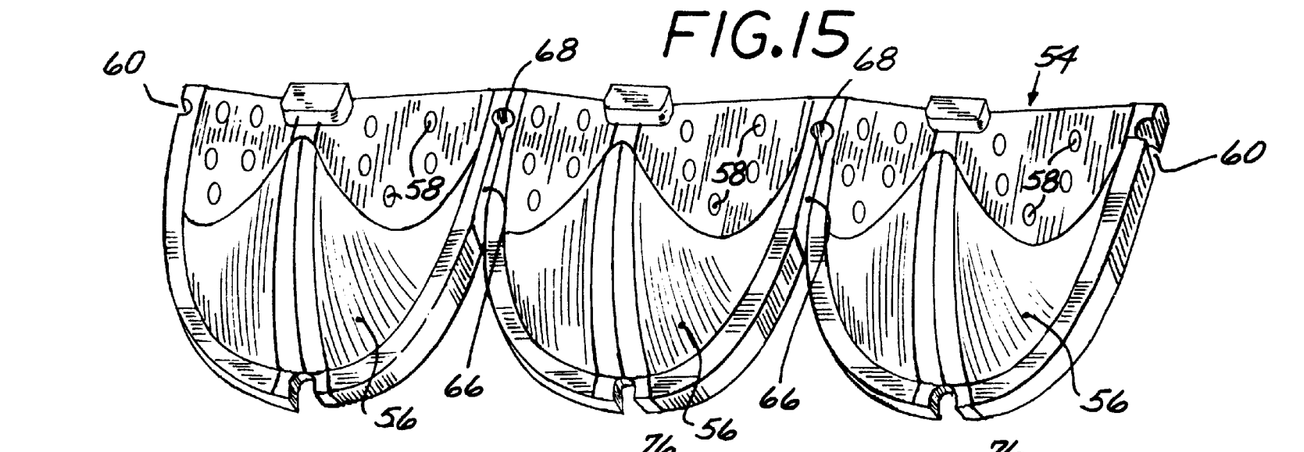
FIG. 15 is a perspective view of the first preferred embodiment of the negative template of FIG. 9.
Figure 16:
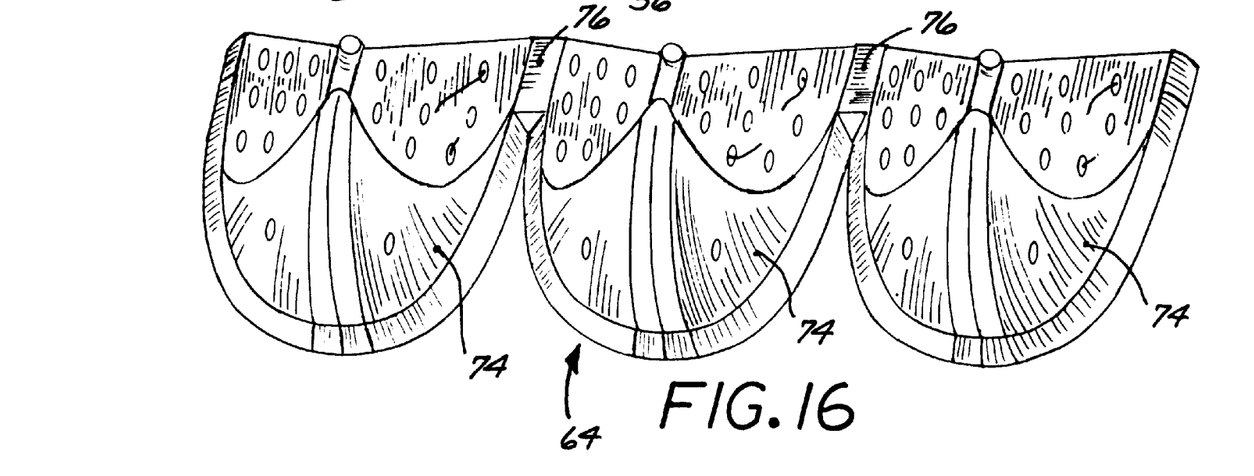
FIG. 16 is a perspective view of the first preferred embodiment of the positive template of FIG. 12.
Figure 18:
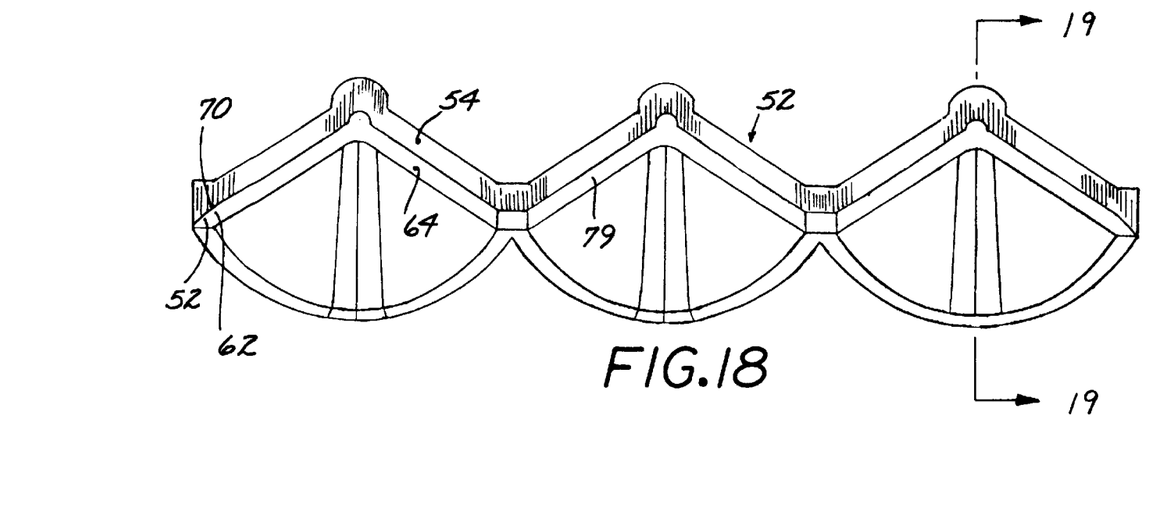
FIG. 18 is a front plan view showing the first preferred embodiment of the positive template of FIG. 9 and the first preferred embodiment of the negative template of FIG. 12 assembled to one another.

As shown in FIGS. 11 and 18, the interior or lower surface of the edge of the negative template 54 includes a substantially flat 70 strip of less than approximately 2 mm in width. This provides area for suturing the molded heart valve into the natural heart valve root (not shown).

Figure 17:
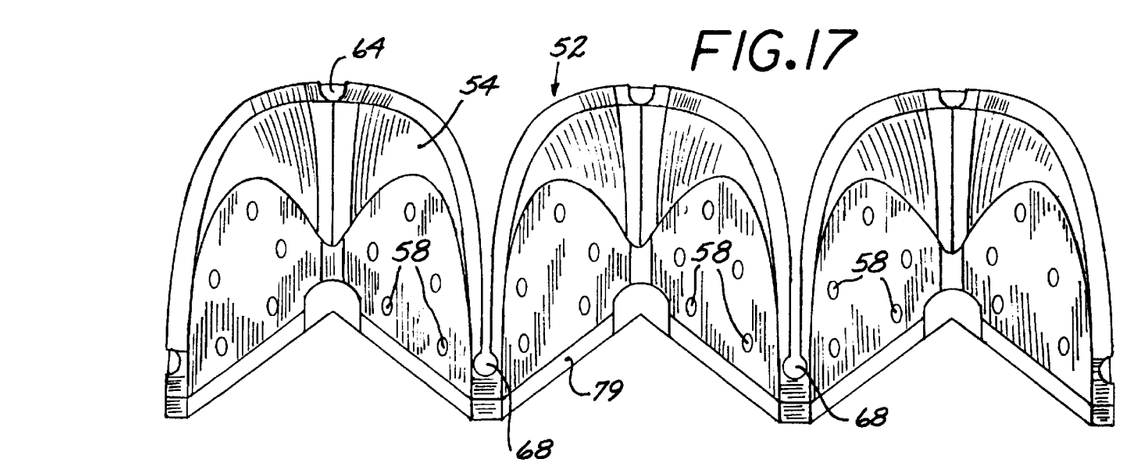
FIG. 17 is a top plan view showing the first preferred embodiment of the negative template of FIG. 9 and the first preferred embodiment of the positive template of FIG. 12 assembled to one another.

FIGS. 12, 13, 14 and 16 illustrate in detail the positive template 64 of the mold 52. The positive template 64 is also an integrally fabricated (preferably by injection molding) thin shell of substantially uniform thickness. The thin shell positive template 64 is also comprised of three members or cusps 74 which are joined together with substantially flat narrow connecting strips 76. The thin shell of the positive template 64 also includes a plurality of holes or perforations 78, which are, however preferably not aligned with the holes 58 of the negative template 54. The relative dispositions of the perforations 58 and 78 allow a treating or tanning solution to seep through and effectively wet and treat the biological membrane enclosed in the mold. The positive template 64 is also beveled in the edges as is shown in FIG. 17 and indicated with the reference numeral 79. The bevels on the edges of the negative template 54 and the positive template 64 are opposite to one another so that in the assembled mold 52 they come together in an acute angle.

A feature unique to the first preferred embodiment of the mold is the presence of a small protrusion or knob 79a at the apex of both the negative 54 and positive 64 templates. The purpose of the knob 79a is to duplicate the native anatomical feature of the aortic valve, known as nodule arantius.

Figure 19:
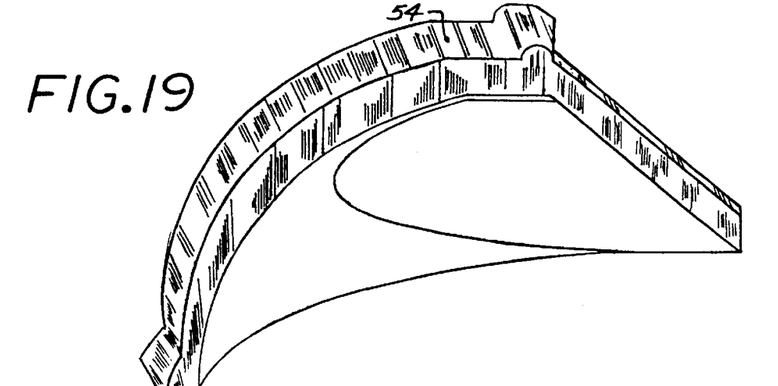
FIG. 19 is a partial cross-sectional view taken on lines 19,19 of FIG. 18.

FIGS. 17, 18, and 19 illustrate the negative template 54 and positive template 64 of the pericardial heart replacement valve mold 52 assembled to one another, so that their respective convex and concave mating surfaces touch or almost touch one another. FIGS. 20 through 23 schematically illustrate how the mold 52 of the present invention is used for fabricating a replacement heart valve from a biological membrane. As it was noted above, the mold 52 of the invention is well suited for fabricating replacement heart valves from autologous, homologous or heterologous biological membrane tissue. In each instance of using any one of these tissues, it is necessary to treat the tissue with a tanning or other type of treating solution to change the consistency of the tissue, to conform it to the configuration dictated by the mold and to cause the tissue to substantially retain that configuration. As it is known in the prior art, one type of tanning solution for this purpose contains an aldehyde, preferably glutaraldehyde, which destroys all living cells in the tissue and causes cross-linking in the tissue. The mold 52 of the present invention is suitable for use in conjunction with this type of glutaraldehyde-containing or other prior art tanning solution.

A presently contemplated preferred use of the mold 52 is with autologous tissue, for example pericardium, that is obtained from the patient while cardiac surgery is in progress, and which can be fabricated quickly, accurately and efficiently into a replacement heart valve in the mold 52 with the use of a liquid composition that contains the following ingredients: approximately 10 to 70% by volume of a water-miscible non toxic polar solvent, such as ethyl alcohol, approximately 2 to 30% by weight of polyethylene glycol of a molecular weight between approximately 6,000 to 15,000 D, and approximately 0.01 to 1.0% by weight of heparin, the rest of the liquid composition consisting substantially of water. A preferred embodiment of the liquid composition that is preferably used in conjunction with the mold of the present invention contains: approximately 50% by volume ethanol, approximately 5% by volume of polyethylene glycol having a molecular weight of approximately 8,000 D, and approximately 0.5% heparin, the rest of the composition consisting substantially of water.

Figure 20:
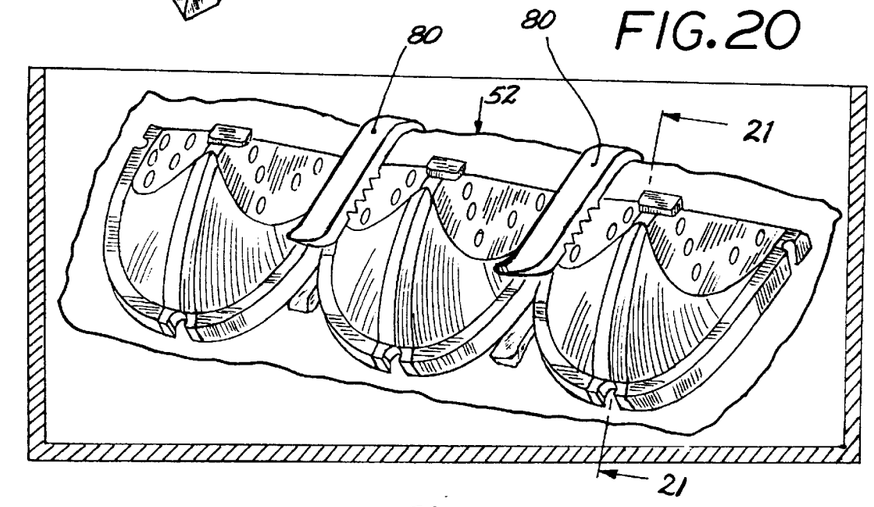
FIG. 20 is a view showing the assembled mold of FIG. 18 having autologous tissue and immersed in a solution in accordance with the present invention.
Figure 21:
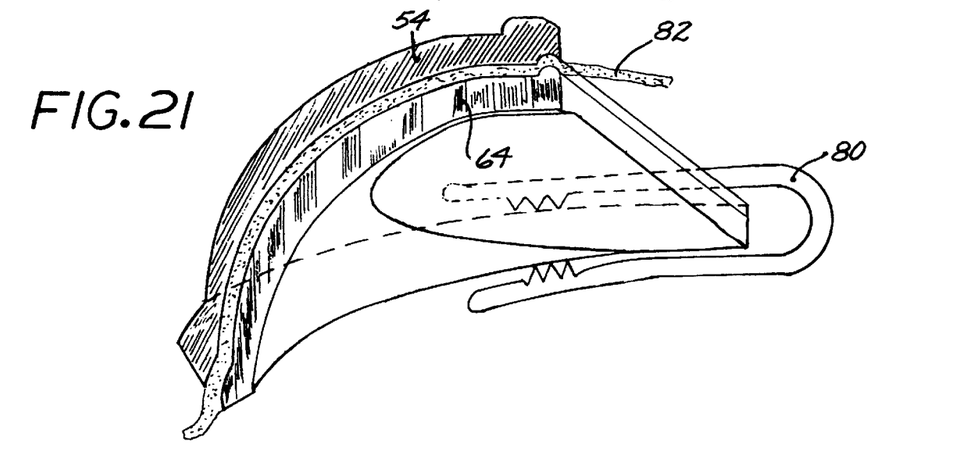
FIG. 21 is a partial cross sectional view of the mold with autologous tissue, the cross-section being taken on lines 21,21 of FIG. 20.

In this presently preferred mode of using of the mold 52 of the invention, fresh pericardium, obtained from the patient who is undergoing open-heart surgery, is placed into the mold 52. The two parts or templates 54 and 64 of the mold 52 are held together with clips 80, shown in FIG. 20. The mold 52 having the tissue 82 sandwiched between the two templates 54 and 64 is submerged in the above described composition for approximately 2 to 8 minutes. This is schematically illustrated in FIG. 20. Instead of the clips 80, other mechanical devices such as bolts, or springs can be used to hold the two templates together. However, because the process of using the mold must be performed quickly, easy to put on and easy to remove means of fastening, such as the clips 80, offer an advantage.

Figure 22:
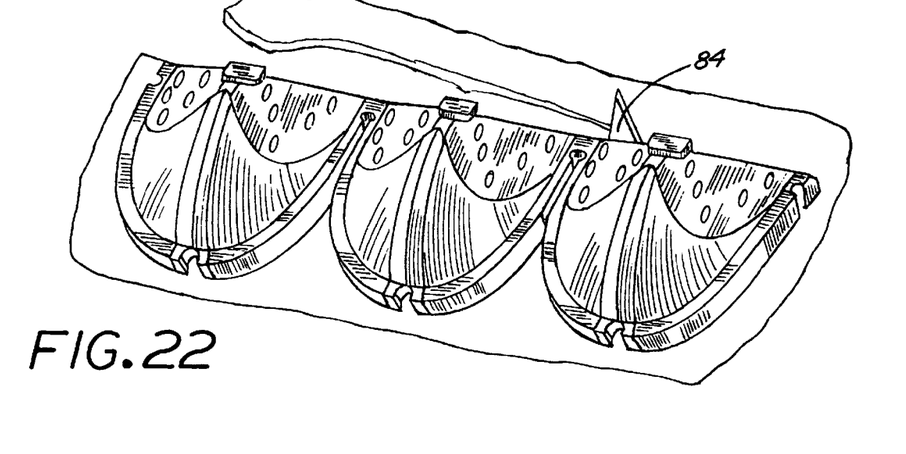
FIG. 22 is a partial schematic view, schematically showing the trimming of excess autologous tissue to form a replacement heart valve, in accordance with the present invention.
Figure 23:
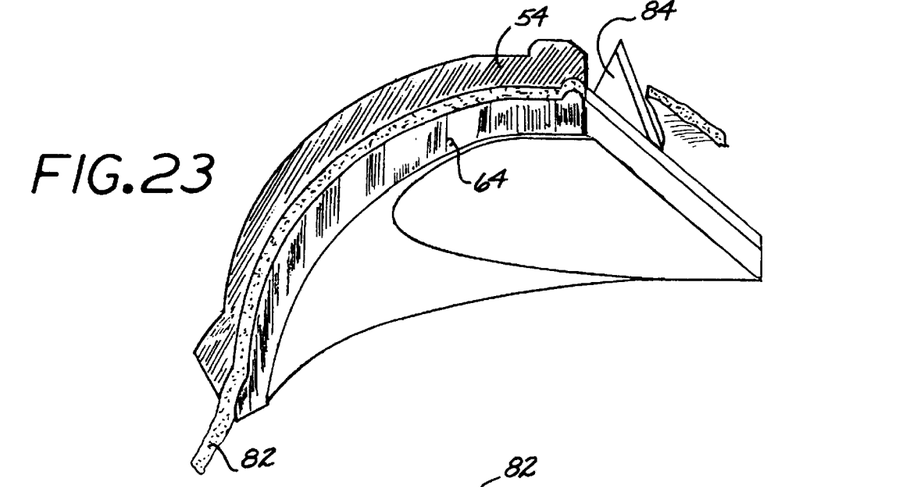
FIG. 23 is a cross-sectional view taken on lines 23,23 of FIG. 22.
Figure 24:
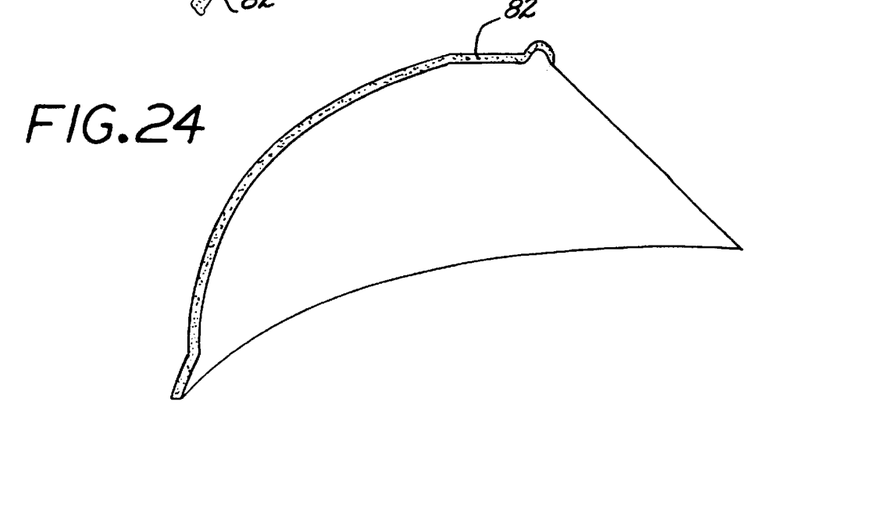
FIG. 24 is a partial cross sectional view of the trimmed autologous tissue.

During submersion the liquid composition percolates through the tissue 82 and modifies its tissue reactivity and renders the tissue temporarily more rigid than in its natural state, thereby making it more easy to handle. After the 2 to 8 minutes long submersion in the liquid composition the tissue 82 is trimmed with a surgical knife along the edges of the mold 52. Because the mold 52 is made of two templates 54 and 64 of thin shell construction, and because of the above-described and illustrated shape of the mold 52, especially the bevelled edges that form an acute angle in area 79 of the assembled mold 52, the surgical knife can come very close to the tissue. This renders possible precise, effective and quick trimming. The trimming process is schematically illustrated in FIG. 22, where the surgical knife bears the reference numeral 84.

After the trimmed tissue 82 is removed from the mold 52, its is noticeably more rigid and easier to handle than the native tissue. The two loose ends of the trimmed tissue are attached to one another to form the heart valve (not shown). The replacement heart valve (not shown) molded in this manner is placed into the heart (not shown) by suturing into the valve root (not shown). The valve molded in this manner from autologous tissue and treated with the preferred liquid composition quickly regains the physical characteristics of the native tissue, after being rinsed with saline, or being exposed to physiological solutions such as the patient's blood. The molded valve functions just as the natural valve in opening and closing phase. In the closing position the molded cusps fold back to seal and prevent back-flow or leakage in the rearward direction. In the open position, the molded cusps fold out to their maximum to allow free flow of blood across the replacement valve. It should be readily apparent from the foregoing that the mold of the present invention is not an implantable device but a tool for forming implantable heart valve replacements from biological membranes. The thin shell construction of the mold makes the trimming process, that is the final shaping of the heart valve, accurate and more easily performed than the procedures employed in the prior art. In this regard these bevelled edges of the template play a particularly advantageous role. The perforations in the templates play the advantageous role of allowing effective fluid flow and percolation of the tissue when the tissue is exposed in the mold to a treating solution. The grooves contained in the positive mold allow the surgeon to identify the highest and lowest points of commisures and ease the suturing process.

Figure 25:
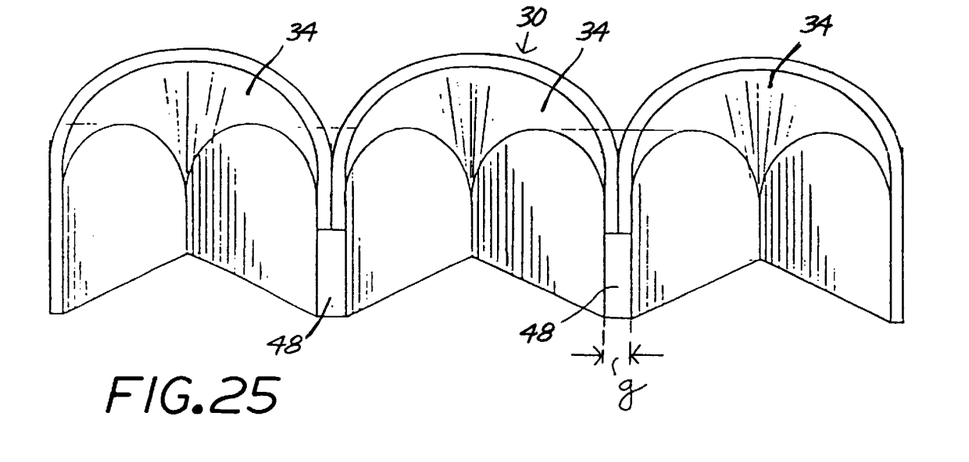
FIG. 25 is a schematic top plan view showing the general configuration of three negative cusps of second preferred embodiment assembled to form a negative template used for shaping an aortic valve replacement from autologous tissue, utilizing the novel solution and method of the present invention.

Referring now to FIGS. 25–27 a second preferred embodiment of the mold is disclosed through the drawings which illustrate the negative template 30 if this embodiment. Principal differences between the second preferred embodiment and the previously described first preferred embodiment is that the second preferred embodiment lacks the protrusion or knob 79a of the first preferred embodiment, and also in that it lacks the curved extension of the commissure 86 of the first preferred embodiment which in the first preferred embodiment is designed to meet the edge of the aortic root (not shown).

The molds of the invention may be made inexpensive enough to be considered disposable, in the sense that each mold may be used only once in a single heart valve replacement operation where the mold has been custom-fabricated for the patient. Alternatively, a number of molds of varying sizes may be provided, from among which the one of appropriate size is chosen for any given patient.

FIGS. 28 through 33 disclose a first embodiment of a sizing device or sizer 88 that is used to determine, under certain circumstances, whether or not the surgical procedure of valve replacement in accordance with the present invention is appropriate for a given patient, and also to select the appropriate mold for a particular patient. As is shown, the sizing device or sizer 88 is a body configured as a sphere truncated at two opposite ends, and with a hole 90 or other means to attach a rod 92 that serves as a handle. The truncated spherical body of the sizer 88 can be made practically from any material that can be sterilized and is biocompatible in the sense that it can be brought into temporary contact with living tissue. Medical grade plastic is the preferred material presently contemplated for the valve sizer. The rod 92 that is attached as a handle is preferably stainless steel, although the rod 92 can also be made of medical grade plastic.

Three grooves or markers 94 are placed at 120° apart from one another on the exterior of the sizer 88 so as to divide the spherical, or truncated spherical body of the sizer 88 into three equal segments. When the diameter of the spherical body of the sizer is d, then the width x of each groove or marker is in the range of $0.08\ d < x < 0.2\ d$. Ideally the width of each groove is approximately 3% of the circumference of the sphere. The sizer 88 is used in the following manner. During cardiac surgery, after the surgeon has excised the patient's diseases aortic valve, an orifice (not shown) is created by the excision to which the replacement aortic valve will be sutured during the rest of the surgical procedure. Numerous sizers 88 with diameters (d) ranging from 15 mm to 33 mm are provided and are made available to the operating surgeon (not shown). The surgeon then measures the diameter of the aortic valve replacement that would be appropriate for the patient (not shown) by finding the sizer 88 that fits best within the orifice (not shown) created by the excision. This is done by gently pushing the spherical body of the sizer 88 into the orifice (not shown) while it is held by the rod 92, to determine which sizer provides a tight but comfortable fit. The diameter (d) of the sizer that fits indicates the diameter of the patient's valve root annulus.

It is known that there is a variability in the location of aortic valve commissures among patients, and in some cases the different distances between commissures is so significant that the proposed surgical technique of aortic valve reconstruction would not be considered valid or proper. The grooves or markers 94 have the width indicated above. After having determined with the sizer 88 the diameter of the patient's valve root annulus thereby enabling the selection of the appropriately sized mold to form the aortic valve replacement, the surgeon attempts to align the markers 94 of the sizer 88 with the aortic commissures of the patient. If the commissures are not located within the markers 94, then that is an indication that for this particular patient the contemplated aortic valve replacement is unlikely to be appropriate, and that an alternative surgical technique is advisable.

Because the sizers are made from medical grade plastic they are generally considered disposable, and are used only a single time. It should be readily apparent from the foregoing that the sizer 88 does not need to comprise a solid body, but can be hollow. Moreover, it is not necessary for the sizer to be spherical, a cylindrical body with ribs or markers separated at 120° from each other would also be suitable. However, the use of a spherical, or truncated spherical body is advantageous, because a spherical body does not need to be axially aligned with the orifice that has been created with the excision while a cylindrical body would have to be axially aligned to give an accurate measurement.

What is claimed is:

1. A mold for forming substantially flat biological membranes into a configuration suited for forming a replacement tissue heart valve, the mold comprising:

a first template comprising a first, a second and a third cusp, the second cusp being laterally joined to the first cusp by a narrow band of material, and the third cusp being laterally joined to the second cusp by a narrow band of material, each cusp having a concave surface, the three joined cusps thereby forming a substantially hollow concave surface with three distinct cavities, and a second template comprising a first, a second and a third cusp, the second cusp being laterally joined to the first cusp by a narrow band of material, and the third cusp being laterally joined to the second cusp by a narrow band of material, each cusp having an exterior convex surface, the concave and convex surfaces of the first and second templates being configured to mate with one another whereby the second template can be fitted to tightly abut against the first template with the cusps of the second template fitted in the cavities formed in the first template, the abutting concave and convex mating surfaces of the first and second templates also being configured in the shape adapted for forming a replacement tissue heart valve.

2. The mold of claim 1 wherein each template further comprises a plurality of aperture whereby a liquid may penetrate to a thin flat membrane that may be placed between the mating surfaces of the first and second templates to form said replacement tissue heart valve.

3. The mold of claim 1 further comprising means for holding the first and second templates together with their respective mating surfaces abutting each other.

4. The mold of claim 1 wherein the narrow bands of the first template include a slot that permits entry of a surgical knife into the slot.

5. The mold of claim 4 wherein each slot terminates in a substantially round aperture that is substantially wider than the slot.

6. The mold of claim 1 wherein the first template has a narrow peripheral skirt including a flat area that in the molded biological membrane provides an area for placing sutures.

7. The mold of claim 6 wherein each template includes bevelled edges, the bevels of the first and second templates being disposed in opposite directions so that in the assembled templates the bevelled edges form an acute angle, whereby a biological membrane fitted between the templates can be precisely trimmed to conform to the shape of the mold.

8. The mold of claim 6 wherein the peripheral skirt includes a plurality of indentations that provide a mark in the biological membrane placed in the mold.

9. A mold for forming substantially flat biological membranes into a configuration suited for forming a replacement tissue heart valve, the mold comprising:

a first template comprising a first, a second and a third cusp, each cusp including an inferior concave surface, a narrow substantially flat band on one lateral side, and a narrow skirt that includes a flat area, and a plurality of apertures that penetrate through each cusp from its superior surface to the inferior concave surface, the second cusp being laterally joined to the first cusp by the narrow band of material, and the third cusp being laterally joined to the second cusp by a narrow band of material, the three joined cusps thereby forming a substantially hollow concave surface with three distinct cavities, a second template comprising a first, a second and a third cusp, each cusp including a superior convex surface, a narrow substantially flat band on one lateral side, and a narrow skirt that includes a flat area, and a plurality of apertures that penetrate through each cusp from its superior convex surface to the inferior surface, the second cusp being laterally joined to the first cusp by the narrow band, and the third cusp being laterally joined to the second cusp by a narrow band of material, the three joined cusps thereby forming a substantially convex surface, the concave and convex surfaces of the first and second templates being configured to mate with one another whereby the second template can be fitted to tightly abut against the first template with the cusps of the second template fitted in the cavities formed in the first template, the abutting concave and convex mating surfaces of the first and second templates also being configured in the shape adapted for forming a replacement tissue heart valve.

10. The mold of claim 9 further comprising means for holding the first and second templates together with their respective mating surfaces abutting each other.

11. The mold of claim 9 wherein the narrow bands of the first template include a slot that permits entry of a surgical knife into the slot.

12. The mold of claim 11 wherein the slot terminates in a substantially round aperture that is substantially wider than the slot.

13. The mold of claim 9 wherein each template includes bevelled edges, the bevels of the first and second templates being disposed in opposite directions so that in the assembled templates the bevelle edges form an acute angle, whereby a biological membrane fitted between the templates can be precisely trimmed to conform to the shape of the mold.

14. The mold of claim 9 wherein the mating surfaces of the first and second templates define three substantially identical curved surfaces, with each curved surface having curvature that includes a first curve in the x and y coordinates of space that is defined by the equation $$x^2/a^2 + y^2/b^2 = 1$$

where a has a value greater than zero and less than 22.0 (0<a<22.0), and b has a value greater than zero and less than 14.0 (0<b<22.0), and a second curve in the x and z coordinates of space that is defined by the equation $$x^2/a^2 + z^2/c^2 = 1$$

where a has a value greater than zero and less than 14.0 (0<a<22.0), and c has a value greater than zero and less than 12.0 (0<c<22.0).

15. The mold of claim 9 wherein the width of each cusp of the first template is 0.8d' to 1.0d' (0.8d'<d<1.0d') wherein d' represents the diameter of patient's valve root annulus for whom the mold is utilized to form a replacement heart valve.

16. The mold of claim 9 wherein the width of the narrow band of the first template is between approximately 0.05 to 0.12 d' (0.05 d'<g <0.12d'), where d' represents the diameter of a patient's valve root annulus for whom the mold is utilized to form a replacement heart valve.

17. The mold of claim 14 wherein the width of each cusp of the first template is 0.8d' to 1.0d' (0.8d'<d<1.0d') wherein d' represents the diameter of a patients's valve root annulus for whom the mold is utilized to form a replacement heart valve.

18. The mold of claim 17 wherein the width of the narrow band of the first template is between approximately 0.05 to 0.12 d' (0.05 d'<g<0.12d').

19. The mold of claim 18 wherein each template includes bevelled edges, the bevels of the first and second templates being disposed in opposite directions so that in the assembled templates the bevelled edges form an acute angle, whereby a biological membrane fitted between the templates can be precisely trimmed to conform to the shape of the mold.

20. The mold of claim 19 further comprising means for holding the first and second templates together with their respective mating surfaces abutting each other.

* * * * *